United States Patent
Old

(10) Patent No.: US 9,637,477 B2
(45) Date of Patent: May 2, 2017

(54) THERAPEUTIC SUBSTITUTED PYRROLES

(71) Applicant: Allergan, Inc., Irvine, CA (US)

(72) Inventor: David W. Old, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 29 days.

(21) Appl. No.: 14/716,478

(22) Filed: May 19, 2015

(65) Prior Publication Data

US 2015/0336940 A1    Nov. 26, 2015

Related U.S. Application Data

(60) Provisional application No. 62/000,951, filed on May 20, 2014.

(51) Int. Cl.
| | |
|---|---|
| *C07D 409/06* | (2006.01) |
| *A61Q 7/00* | (2006.01) |
| *A61Q 5/00* | (2006.01) |
| *A61K 8/49* | (2006.01) |

(52) U.S. Cl.
CPC .............. *C07D 409/06* (2013.01); *A61K 8/49* (2013.01); *A61Q 5/00* (2013.01); *A61Q 7/00* (2013.01)

(58) Field of Classification Search
None
See application file for complete search history.

(56) References Cited

U.S. PATENT DOCUMENTS

| | | |
|---|---|---|
| 6,437,146 B1 | 8/2002 | Hattori et al. |
| 7,985,765 B2 | 7/2011 | Old |

OTHER PUBLICATIONS

Berge, S., et al., Pharmaceutical Salts, J. Pharma. Sci. 1977, 66: 1-19, 1.
Carey, F., Organic Chemistry, McGraw-Hill Co., New York, 1987, pp. 11-13.
Silverman, Richard B., Prodrugs and Drug Delivery Systems, Organic Chemistry of Drug Design and Drug Action, 2d Ed., Elsevier Academic Press: Amsterdam, 2004, pp. 496-557.
Heidenreich, R., et al., Angiogenesis: The New Potential Target for the Therapy of Psoriasis?, Drug News Perspect 2008, 21:97-105, 2.

*Primary Examiner* — Matthew Coughlin
*Assistant Examiner* — Po-Chih Chen
(74) *Attorney, Agent, or Firm* — Jonathan Bass

(57) ABSTRACT

Disclosed herein are compounds of the formula:

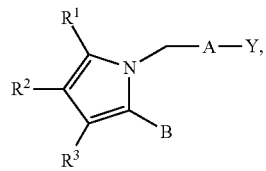

compositions thereof, and methods for the treatment of glaucoma, reducing intraocular pressure, and other prostaglandin $EP_2$ mediated disease and disorders.

11 Claims, No Drawings

THERAPEUTIC SUBSTITUTED PYRROLES

CROSS REFERENCE TO RELATED APPLICATIONS

This application is a non-provisional application which claims the benefit of U.S. provisional application No. 62/000,951, filed on May 20, 2014, which is incorporated by reference herein in its entirety.

FIELD OF THE INVENTION

The invention relates generally to compounds and methods for the treatment of glaucoma, reducing intraocular pressure, and other prostaglandin $EP_2$ mediated disease and disorders.

BACKGROUND

Prostaglandin $EP_2$ selective agonists are useful for treating glaucoma, reducing intraocular pressure, and are believed to have several other medical uses. For example, U.S. Pat. No. 6,437,146 teaches the use of prostaglandin $EP_2$ selective agonists for treating or preventing inflammation, pain in joint and muscle, inflammatory skin and eye conditions, conditions of the gastrointestinal tract associated with inflammation, and other related diseases and disorders Certain therapeutic substituted pyrroles have been described in U.S. Pat. No. 7,985,765. There remains a need for additional therapeutic compounds useful for reducing intraocular pressure, treating glaucoma or intraocular pressure, growing hair, or improving the appearance of hair in mammals, including human beings.

SUMMARY OF THE INVENTION

Disclosed herein are compounds represented by the formula:

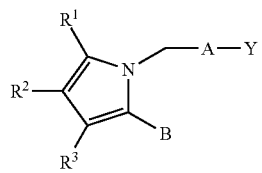

or a pharmaceutically acceptable salt thereof, wherein Y is $C_{0-14}H_{1-30}O_{1-4}S_{0-2}N_{0-4}P_{0-1}$ and is: an organic acid functional group, or an amide or ester thereof; hydroxymethyl or an ether thereof; or a tetrazolyl functional group;
A is —$(CH_2)_5$—, —$CH=CH(CH_2)_3$—, or —$C\equiv C(CH_2)_3$—, wherein:
a) one or two —$CH_2$— groups may be replaced with —O— or —S—, or
b) —$CH_2CH_2$—, —$(CH_2)_3$—, or —$(CH_2)_4$— is replaced by —Ar— and one —$CH_2$— group may be replaced by —O— or —S—;
Ar is aryl of formula $C_{3-10}H_{0-23}N_{0-4}O_{0-4}S_{0-4}F_{0-5}Cl_{0-3}Br_{0-3}I_{0-3}$;
$R^1$, $R^2$, and $R^3$ are each independently —H, —F, —Cl, —Br, —I, or a moiety of a formula $C_{0-6}H_{0-14}N_{0-1}O_{0-2}S_{0-1}$; and
B is aryl of a formula $C_{5-20}H_{0-45}N_{0-4}O_{0-4}S_{0-4}F_{0-5}Cl_{0-3}Br_{0-3}I_{0-3}$.

The compounds provided herein are useful for reducing intraocular pressure, treating glaucoma or intraocular pressure, growing hair, or improving the appearance of hair in mammals, including human beings.

Growing hair includes increasing the length or radius of individual hairs as well as increasing the number of hairs present in a given area. Improving the appearance of hair includes improving the color, such as darkening, or improving its gloss, shine, or other properties related to the reflection, absorption, emission, or dispersion of light.

DETAILED DESCRIPTION

Disclosed herein are compounds represented by the formula:

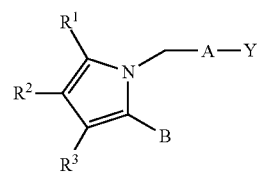

wherein Y is $C_{0-14}H_{1-30}O_{1-4}S_{0-2}N_{0-4}P_{0-1}$ and is: an organic acid functional group, or an amide or ester thereof; hydroxymethyl or an ether thereof; or a tetrazolyl functional group;
A is —$(CH_2)_5$—, —$CH=CH(CH_2)_3$—, or —$C\equiv C(CH_2)_3$—, wherein:
a) one or two —$CH_2$— groups may be replaced with —O— or —S—, or
b) —$CH_2CH_2$—, —$(CH_2)_3$—, or —$(CH_2)_4$— is replaced by —Ar— and one —$CH_2$— group may be replaced by —O— or —S—;
Ar is aryl of formula $C_{3-10}H_{0-23}N_{0-4}O_{0-4}S_{0-4}F_{0-5}Cl_{0-3}Br_{0-3}I_{0-3}$;
$R^1$, $R^2$, and $R^3$ are each independently —H, —F, —Cl, —Br, —I, or a moiety of a formula $C_{0-6}H_{0-14}N_{0-1}O_{0-2}S_{0-1}$; and
B is aryl of a formula $C_{5-20}H_{0-45}N_{0-4}O_{0-4}S_{0-4}F_{0-5}Cl_{0-3}Br_{0-3}I_{0-3}$.

The compounds provided herein are useful for reducing intraocular pressure, treating glaucoma or intraocular pressure, growing hair, or improving the appearance of hair in mammals, including human beings. Growing hair includes increasing the length or radius of individual hairs as well as increasing the number of hairs present in a given area. Improving the appearance of hair includes improving the color, such as darkening, or improving its gloss, shine, or other properties related to the reflection, absorption, emission, or dispersion of light. Thus, provided herein are pharmaceutical compositions, with or without one or more pharmaceutically acceptable excipients, for the above uses. In some embodiments, the pharmaceutical compositions are formulated for oral or topical administration, such that the pharmaceutically acceptable excipients are selected from those relevant to such methods of administration.

Unless otherwise indicated, reference to a compound should be construed broadly to include the compound and pharmaceutically acceptable salts, prodrugs, tautomers, alternate solid forms, non-covalent complexes, and combinations thereof, of a chemical entity of a depicted structure or chemical name.

Any description of a compound made herein is not intended to encompass compounds having structural features that violate the basic principles of chemistry such as containing an atom having too many or too few electrons in its valence shell (see Francis A. Carey, *Organic Chemistry*, McGraw-Hill Book Company: New York, 1987, pp. 11-13). It is also not intended to encompass compounds that are too reactive or otherwise too unstable to be useful as described herein. For example, it is not intended to encompass compounds that cannot either: 1) be put into a bottle with an excipient for subsequent use in treating a mammal as disclosed herein, or 2) be put into a bottle as a salt or a prodrug of the compound with an excipient for subsequent use in treating a mammal as disclosed herein.

Unless otherwise indicated, if a term is used to describe more than one structural feature of the compounds disclosed herein, it should be assumed that the term has the same meaning for all of those features. Similarly, a subgroup of that term applies to every structural feature described by that term.

Unless stereochemistry is explicitly and unambiguously depicted, a structure is intended to include every possible stereoisomer, both pure or in any possible mixture.

"Treat," "treating," or "treatment" refer to the use of a compound, composition, therapeutically active agent, or drug in the cure, mitigation, treatment, or prevention (e.g. prophylactic administration) of disease or other undesirable condition.

A pharmaceutically acceptable salt is any salt of the parent compound that is suitable for administration to an animal or human, or any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring. (See, e.g., *Handbook of Pharmaceutical Salts*, P. Heinrich Stahl & Camille G. Wermuth (Eds), Verlag; *Helvetica Chimica Acta*-Zürich, 2002, 329-345.) The term "pharmaceutically acceptable salt" is also meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66:1-19). Certain specific compounds of the present invention may contain both basic and acidic functionalities that allow the compounds to be converted into either base or acid addition salts.

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —CO$_2$(CH$_2$)$_2$OH,

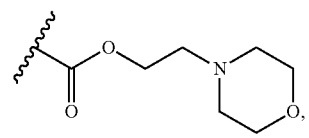 [SMILES: *C(=O)OCCN1CCOCC1]

and the like.

Tautomers are isomers that are in rapid equilibrium with one another. For example, tautomers may be related by transfer of a proton, hydrogen atom, or hydride ion.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species. In these complexes, the compound and the additional chemical species have attractive interactions that are not covalent bonds. Examples include solvates, hydrates, charge transfer complexes, and the like.

An organic acid functional group is an acidic functional group on an organic molecule. For example, organic acid functional groups may comprise an oxide of carbon, sulfur, or phosphorous, such as a carboxylic acid, sulfonic acid, or phosphonic acid functional group.

An amide is a functional group where an —OH of an organic acid is replaced by a nitrogen atom which nitrogen atom is directly attached to: 1) two carbon atoms, 2) two hydrogen atoms, 3) a carbon atom and a hydrogen atom, or 4) a sulfur atom of a sulfonyl (—SO$_2$—) and hydrogen atom.

An ester is a functional group where an —OH of an organic acid is replaced by an oxygen atom which is directly attached to a carbon atom.

The structures below depict examples different organic acid functional groups and their associated amides and esters.

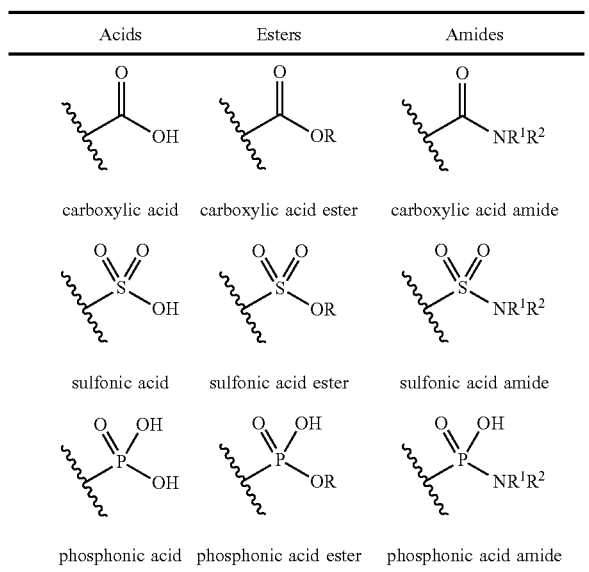

In these examples, R could be alkyl, another hydrocarbyl, or a species such as —CH$_2$CH$_2$OH. R$^1$ and R$^2$ could be hydrogen, alkyl, another hydrocarbyl, or alkyl sulfonyl (i.e. —SO$_2$-alkyl).

Hydrocarbyl is a moiety consisting only of hydrogen atoms and carbon atoms. Examples include:
1. alkyl, which is hydrocarbyl that contains no double or triple bonds, such as:
   a. linear alkyl, e.g. methyl, ethyl, n-propyl, n-butyl, n-pentyl, n-hexyl, etc.,
   b. branched alkyl, e.g. iso-propyl, t-butyl and other branched butyl isomers, branched pentyl isomers, etc.,
   c. cycloalkyl, e.g. cyclopropyl, cyclobutyl, cyclopentyl, cyclohexyl, etc., and
   d. combinations of linear, branched, and/or cycloalkyl;
   $C_{1-3}$ alkyl is alkyl having from 1 to 3 carbon atoms such as methyl, ethyl, propyl, isopropyl, cyclopropyl, etc.
   $C_{1-6}$ alkyl is alkyl having from 1 to 6 carbon atoms such as methyl, ethyl, propyl isomers, butyl isomers, pentyl isomers, hexyl isomers, cyclopropyl, cyclobutyl, cyclopentyl, cyclohexyl, etc.
   $C_{1-10}$ alkyl is alkyl having from 1 to 10 carbon atoms.
2. alkenyl, which is hydrocarbyl having 1 or more double bonds, including linear, branched, or cycloalkenyl;
3. alkynyl, which is hydrocarbyl having 1 or more triple bonds, including linear, branched, or cycloalkynyl;
4. unsubstituted phenyl, naphthyl, etc.; and
5. combinations of alkyl, alkenyl, akynyl; and unsubstituted phenyl, naphthyl, etc.

Hydroxyalkyl is alkyl-OH. For example, hydroxymethyl is —CH$_2$OH.

$C_{1-6}$ hydroxyalkyl is hydroxyalkyl having from 1 to 6 carbon atoms, such as hydroxymethyl, hydroxyethyl isomers, hydroxypropyl isomers, hydroxybutyl isomers, hydroxypentyl isomers, hydroxyhexyl isomers, etc.

$C_{1-10}$ hydroxyalkyl is hydroxyalkyl having from 1 to 10 carbon atoms.

An ether is a moiety comprising an oxygen attached to two different carbon atoms. For example, an ether of hydroxymethyl is —CH$_2$—O-hydrocarbyl. Another example is —O-alkyl.

$C_{1-3}$—O-alkyl is —O-alkyl having 1, 2, or 3 carbon atoms such as —O-methyl, —O-ethyl, —O—C$_3$H$_7$.

$C_{1-10}$—O-alkyl is —O-alkyl having from 1-10 carbon atoms.

$C_{1-3}$—S-alkyl is —S-alkyl having 1, 2, or 3 carbon atoms such as —S-methyl, —S-ethyl, —S—C$_3$H$_7$.

$C_{1-10}$—S-alkyl is —S-alkyl having from 1-10 carbon atoms.

Acyl is

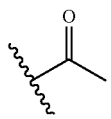 [SMILES: *C(C)=O]

hydrocarbyl.

$C_{1-10}$ acyl is acyl having from 1-10 carbon atoms, such as formyl, acetyl, propionyl, butyryl, pentanoyl, hexanoyl, benzoyl, etc.

A tetrazolyl functional group has one of the tautomeric ring structures below:

The hydrogen on either tautomeric form may be replaced by a substituent as well. These moieties are also considered to be tetrazolyl functional groups.

Aryl is an unsubstituted or substituted aromatic ring or aromatic ring system. The ring or ring system atoms could all be carbon. Alternatively, heteroaryl, a subgenus of aryl, has one or more oxygen, sulfur, or nitrogen atoms in the ring or ring system.

Monocyclic aryl is aryl having only one ring.

Unsubstituted aryl refers to aryl with no substituents. Substituted aryl refers to aryl with one or more substituents. If a group is indicated as "aryl" the bond or bonds to that group directly attach to a carbon atom of an aromatic ring, and not to a substituent.

Any group may be a substituent subject to any restrictions placed upon the moiety that the aryl group is a part of. Examples of substituents include:
   hydrocarbyl, as described above
   alkyl-CN, such as —CH$_2$—CN, —(CH$_2$)$_2$—CN; —(CH$_2$)$_3$—CN, and the like;
   Hydroxy, —OH
   hydroxyalkyl, i.e. alkyl-OH, such as hydroxymethyl, hydroxyethyl, and the like;
   polyhydroxyalkyl, i.e. alkyl having more than 1 —OH substituent;
   ether substituents, including —O-alkyl, alkyl-O-alkyl, and the like;
   thioether substituents, including —S-alkyl, alkyl-S-alkyl, and the like;
   amine substituents, including —NH$_2$, —NH-alkyl,-N-alkyl$^1$alkyl$^2$ (i.e., alkyl$^1$ and alkyl$^2$ are the same or different, and both are attached to N), alkyl-NH$_2$, alkyl-NH-alkyl, alkyl-N-alkyl$^1$alkyl$^2$, and the like;
   aminoalkyl, meaning alkyl-amine, such as aminomethyl (—CH$_2$-amine), aminoethyl, and the like;
   ester substituents, including —CO$_2$-alkyl, —CO$_2$-phenyl, etc.;

other carbonyl substituents, including aldehydes; ketones, such as acyl, including, acetyl, propionyl, and benzoyl substituents;

fluorocarbons or hydroflourocarbons such as —CF$_3$, —CH$_2$CF$_3$, etc.; and other nitrogen containing substituents such as —CN and —NO$_2$, other sulfur containing substitutents such as sulfide, sulfonyl or sulfoxide;

aryl;

combinations of the above are also possible, subject to the constraints defined;

Alternatively, a substituent may be —F, —Cl, —Br, or —I.

The terms imidazolyl, pyrrolyl, furanyl, oxazolyl, thiazolyl, thienyl, pyridinyl, and phenyl refer to both the unsubstituted and substituted versions of the monocyclic aryl rings below.

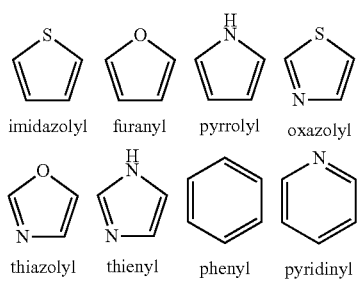

imidazolyl  furanyl  pyrrolyl  oxazolyl thiazolyl  thienyl  phenyl  pyridinyl

Y is $C_{0-14}H_{1-30}O_{1-4}S_{0-2}N_{0-4}P_{0-1}$ and is: an organic acid functional group, or an amide or ester thereof; hydroxymethyl or an ether thereof; or a tetrazolyl functional group.

In any given formula, a subscript containing a range of values such as 0-14, 1-30, etc. indicates the number of that particular atom or group with which it is associated. For example, $C_{0-14}H_{1-30}O_{1-4}S_{0-2}N_{0-4}P_{0-1}$ indicates 0-14 carbon atoms, 1-30 hydrogen atoms, 1-4 oxygen atoms, 0-2 sulfur atoms, 0-4 nitrogen atoms, and 0-1 phosphorous atoms. Similarly $C_{1-10}$ alkyl indicates alkyl characterized by having 1-10 carbon atoms, and

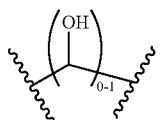

indicates that there are 0 or 1 hydroxymethylene groups (i.e. the group in parenthesis) present.

In one embodiment, Y is —CO$_2$R$^4$, —CONR$^5$R$^6$, —CON(CH$_2$CH$_2$OH)$_2$, —CONH(CH$_2$CH$_2$OH), —CH$_2$OH, —P(O)(OH)$_2$, —CONHSO$_2$R$^4$, —SO$_2$NR$^5$R$^6$

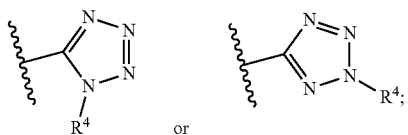

wherein R$^4$, R$^5$ and R$^6$ are independently H, C$_1$-C$_6$ alkyl, C$_{1-6}$ hydroxyalkyl, unsubstituted phenyl, or unsubstituted biphenyl.

In another embodiment, Y is —CO$_2$R$^4$.
In another embodiment, Y is —CO$_2$H, —CO$_2$CH$_3$, —CO$_2$CH$_2$CH$_3$, or —CO$_2$—C$_3$H$_7$.
In another embodiment Y is —CO$_2$(CH$_2$)$_2$OH or

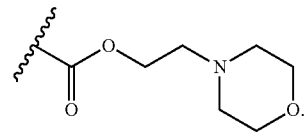 [SMILES: *C(=O)OCCN1CCOCC1]

In another embodiment Y is —CONR$^5$R$^6$.
In another embodiment Y is —CO$_2$R$^5$, wherein R$^5$ is —H or C$_{1-6}$ alkyl.
In another embodiment Y is —CO$_2$R$^5$, wherein R$^5$ is —H or C$_{1-6}$ alkyl.

A is —(CH$_2$)$_5$—, —CH═CH(CH$_2$)$_3$—, or —C≡C(CH$_2$)$_3$—, wherein:

a) 1 or 2 —CH$_2$— may be replaced with —O— or —S—, or b) —CH$_2$CH$_2$—, —(CH$_2$)$_3$—, or —(CH$_2$)$_4$— is replaced by —Ar— and 1 —CH$_2$— may be replaced by —O— or —S—, Ar is aryl of a formula $C_{3-10}H_{0-23}N_{0-4}O_{0-4}S_{0-4}F_{0-5}Cl_{0-3}Br_{0-3}I_{0-3}$, Thus, A may be —(CH$_2$)$_5$—, —CH═CH(CH$_2$)$_3$—, or —C≡C(CH$_2$)$_3$—.

In the case that 1 or 2 —CH$_2$— moieties may be replaced with —O— or —S—, one or two sulfur or oxygen atoms takes the place of a methylene in the alkyl, alkenyl, or alkynyl chain. The structures depicted below are some typical examples of this.

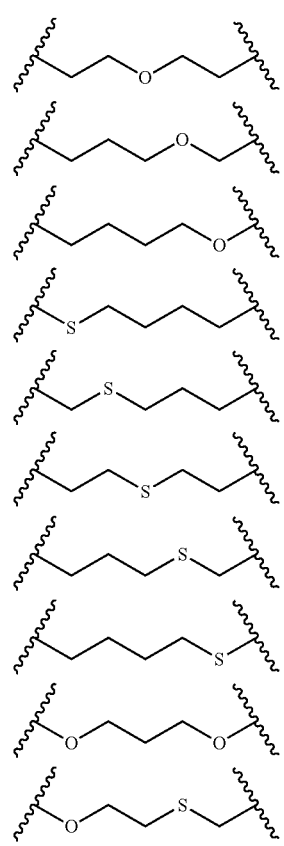

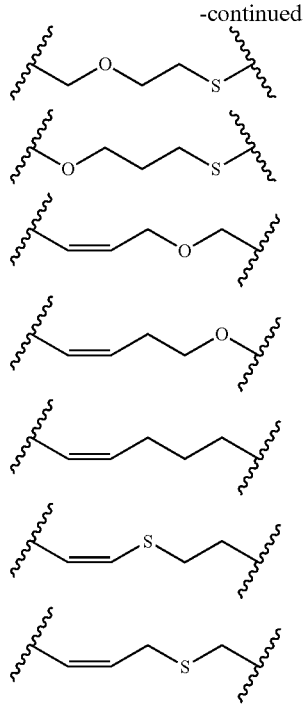
In the case that —CH$_2$CH$_2$—, —(CH$_2$)$_3$—, or —(CH$_2$)$_4$— is replaced by —Ar—, A may be a structure such as one of those shown below.
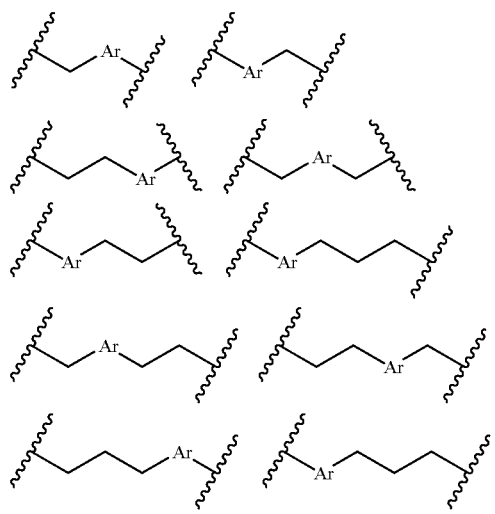
The statement that 1 —CH$_2$— may be replaced by —O— or —S— means that A may be a structure such as one of those shown below.
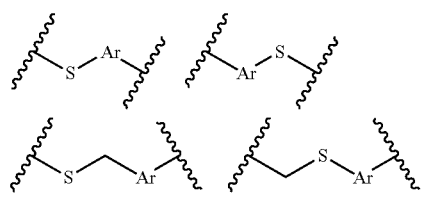
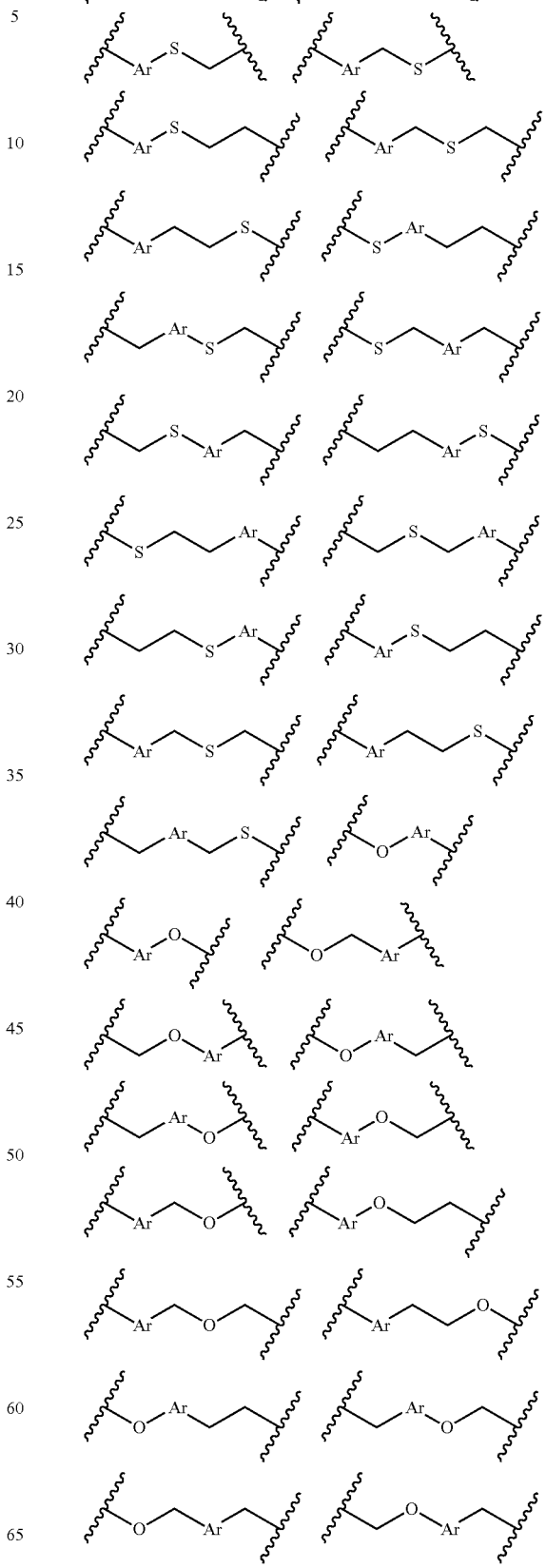

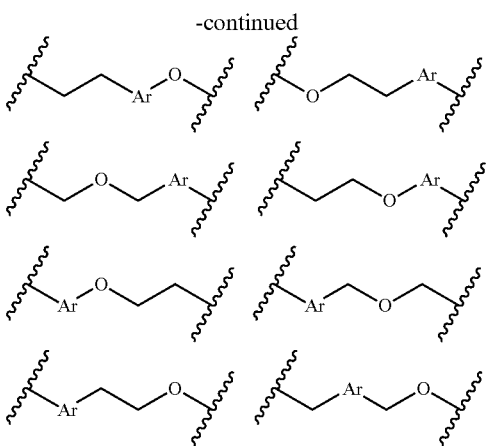

In one embodiment, A is —(CH$_2$)$_5$—, —CH=CH(CH$_2$)$_3$—, or —C≡C(CH$_2$)$_3$—, wherein:
a) 1 or 2 —CH$_2$— may be replaced with —O— or —S—, or
b) 1) a) —CH$_2$CH$_2$— is replaced by 1,2-attached —Ar—,
   b) —(CH$_2$)$_3$— is replaced by 1,3,-attached —Ar—, or
   c) —(CH$_2$)$_4$— is replaced by 1,4-attached —Ar—; and
2) 1 —CH$_2$— may be replaced by —O— or —S—, Examples of A wherein —CH$_2$CH$_2$— is replaced
by 1,2-attached —Ar— and one —CH$_2$— moiety
may be replaced by —O— or —S—

1,2-attached —Ar— indicates that the remainder of the A moiety attaches to —Ar— at two carbons that are adjacent on the ring. In the case of phenyl, this is the same as ortho substitution. For other aryls, 1,2-is the analogous substitution.

Thus, if —CH$_2$CH$_2$— is replaced by 1,2-attached —Ar—, structures such as those shown below are obtained.

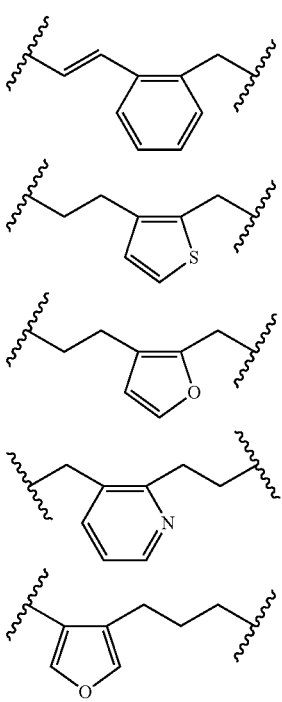

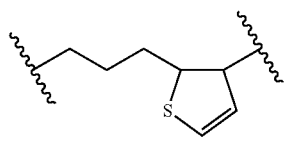

If one of the —CH$_2$— moieties is replaced with S or O, structures such as those shown below may be obtained.

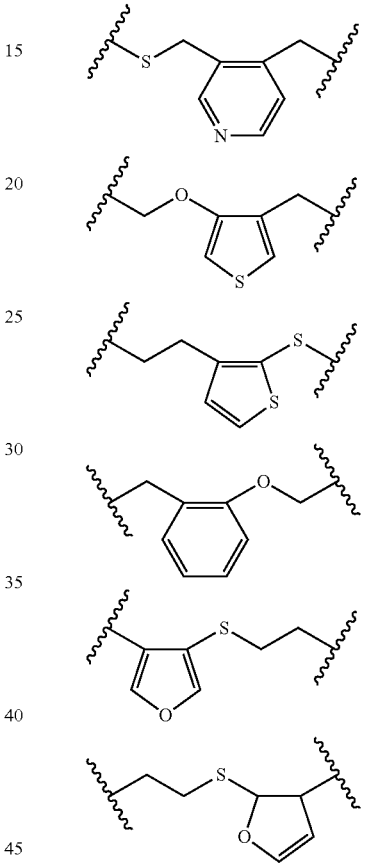

Many other examples are possible by varying the type of aromatic ring, the position of an —O— or —S— (if present), and the position of the ring in the chain structure. Further variation is possible if substituents are present on the aromatic ring.

Examples of A wherein —(CH$_2$)$_3$— is replaced by
1,3-attached —Ar—, and one —CH$_2$— moiety
may be replaced by —O— or —S—

1,3-attached —Ar— indicates that the remainder of the A moiety attaches to carbon atoms on the aromatic ring which are separated by a single aromatic ring atom (e.g. =CH—, —O—, —S—, —N—, etc.). In the case of phenyl, this is the same as meta substitution. For other aryls, 1,3- is the analogous substitution.

Thus, if —(CH$_2$)$_3$— is replaced by 1,3,-attached —Ar—, structures such as those shown below are obtained.

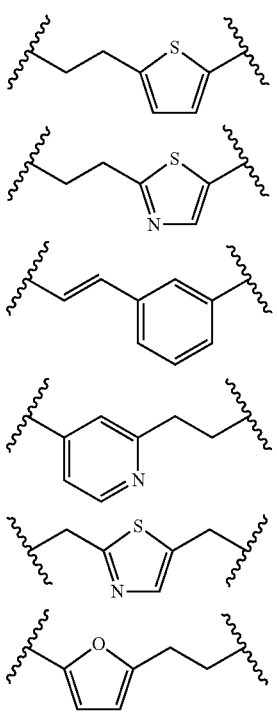

If one of the —CH$_2$— moieties is replaced with S or O, structures such as those shown below may be obtained.

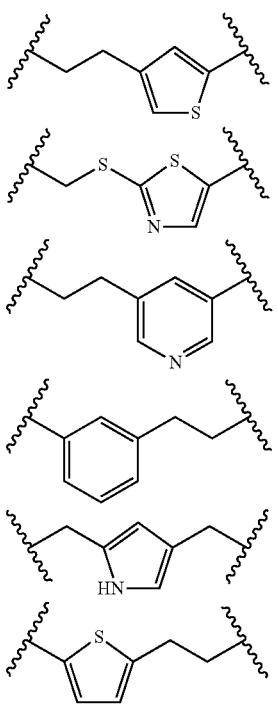

Many other examples are possible by varying the type of aromatic ring, the position of an —O— or —S— (if present), and the position of the ring in the chain structure. Further variation is possible if substituents are present on the aromatic ring.

Examples of A wherein —(CH$_2$)$_4$— is replaced by 1,3,-attached —Ar—, and one —CH$_2$— moiety may be replaced by —O— or —S—

1,4-attached —Ar— indicates that the remainder of the A moiety attaches to carbon atoms on a six-membered aromatic ring (e.g. phenyl or pyridinyl) which are separated by two aromatic ring atoms (e.g. —CH═CH—, —O—CH═, ═CH—S—, —C═N—, etc.). In the case of phenyl, this is the same as para substitution. For other aryls, 1,4- is the analogous substitution.

Thus, if —(CH$_2$)$_3$— is replaced by 1,3,-attached —Ar—, structures such as those shown below are obtained.

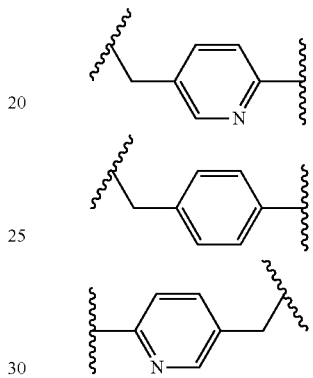

If one of the —CH$_2$— moieties is replaced with S or O, structures such as those shown below may be obtained.

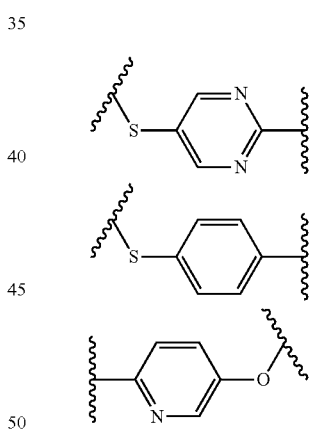

Many other examples are possible by varying the type of aromatic ring, the position of an —O— or —S— (if present), and the position of the ring in the chain structure. Further variation is possible if substituents are present on the aromatic ring.

In other embodiments, A has one of the following structures, wherein Y attaches to the ring.

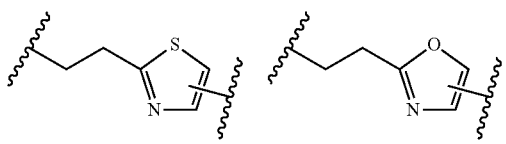

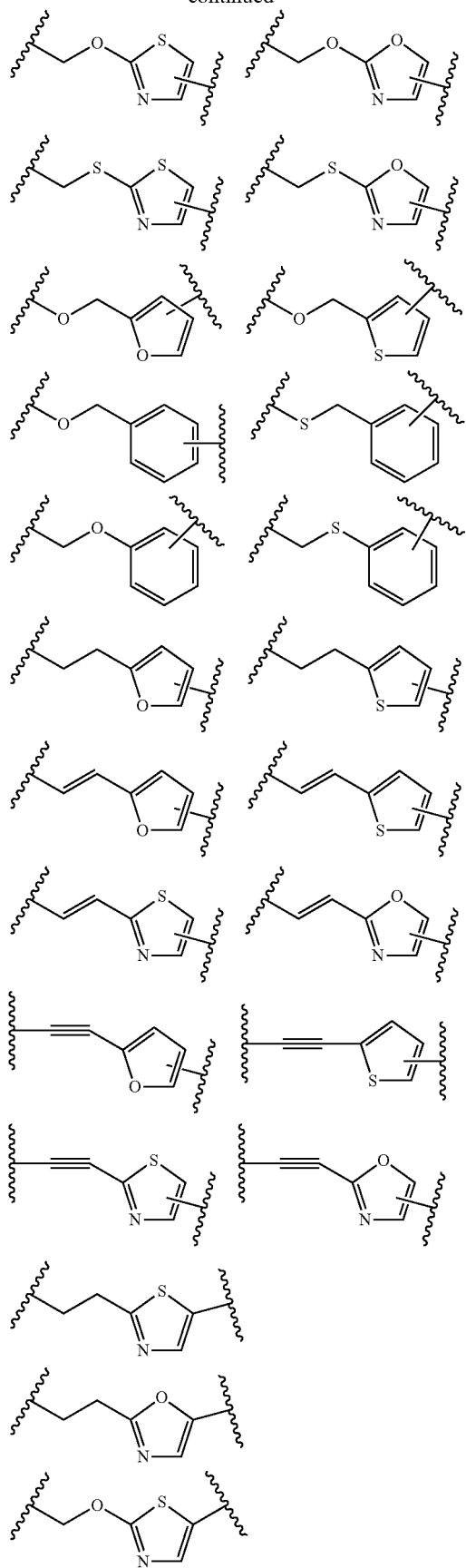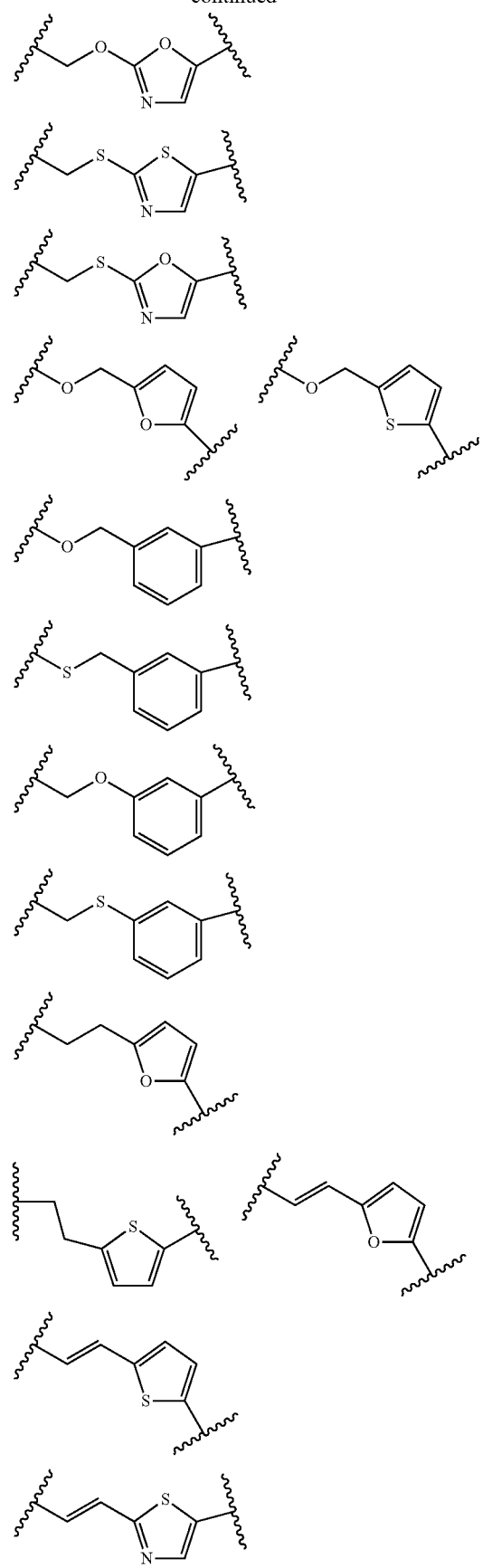

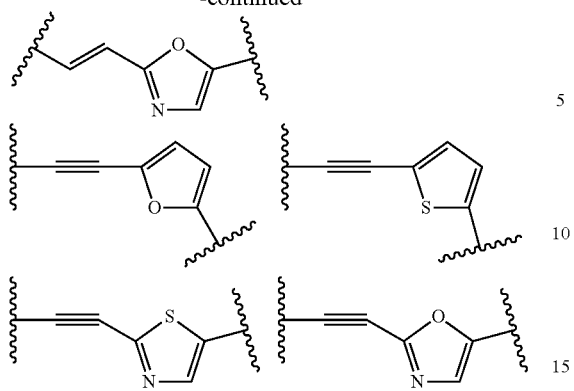

In one embodiment, A is —(CH$_2$)$_3$Ar—, wherein Ar is thienyl.

In one embodiment, A is —(CH$_2$)$_3$Ar—, wherein Ar is 1,3-attached thienyl.

In another embodiment, A is —(CH$_2$)$_2$ArCH$_2$—, wherein Ar is thienyl.

In another embodiment, A is —(CH$_2$)$_2$ArCH$_2$—, wherein Ar is 1,3-attached thienyl.

In another embodiment, A is —CH$_2$Ar(CH$_2$)$_2$—, wherein Ar is thienyl.

In another embodiment, A is —CH$_2$Ar(CH$_2$)$_2$—, wherein Ar is 1,3-attached thienyl.

In another embodiment, A is —(CH$_2$)$_2$Ar—, wherein Ar is thienyl with 1 or 2 substituents selected from —F, —Cl, —Br, —OH, and —OCH$_3$, and 1 —CH$_2$— may be replaced by —O— or —S—.

Another embodiment is a compound represented by a formula:

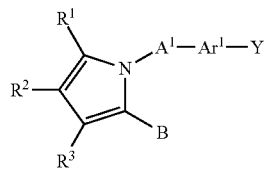

wherein A$^1$ is —(CH$_2$)$_3$—, —O(CH$_2$)$_2$—, —S(CH$_2$)$_2$—, —CH$_2$OCH$_2$—, —CH$_2$SCH$_2$—, —(CH$_2$)$_2$O—, or —(CH$_2$)$_2$S—;

Ar$^1$ is 1,3-attached thienyl, furyl, or pyrrolyl with 0, 1, or 2 substituents selected from, —F, —Cl, —Br, —CH$_3$, or —OCH$_3$.

R$^1$, R$^2$, and R$^3$ are independently —H, —F, —Cl, —Br, —I, or a moiety of a formula C$_{0-6}$H$_{0-14}$N$_{0-1}$O$_{0-2}$S$_{0-1}$.

Thus, compounds such as those examples shown below are possible.

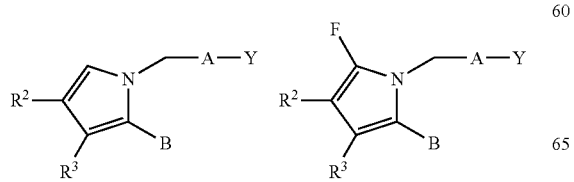

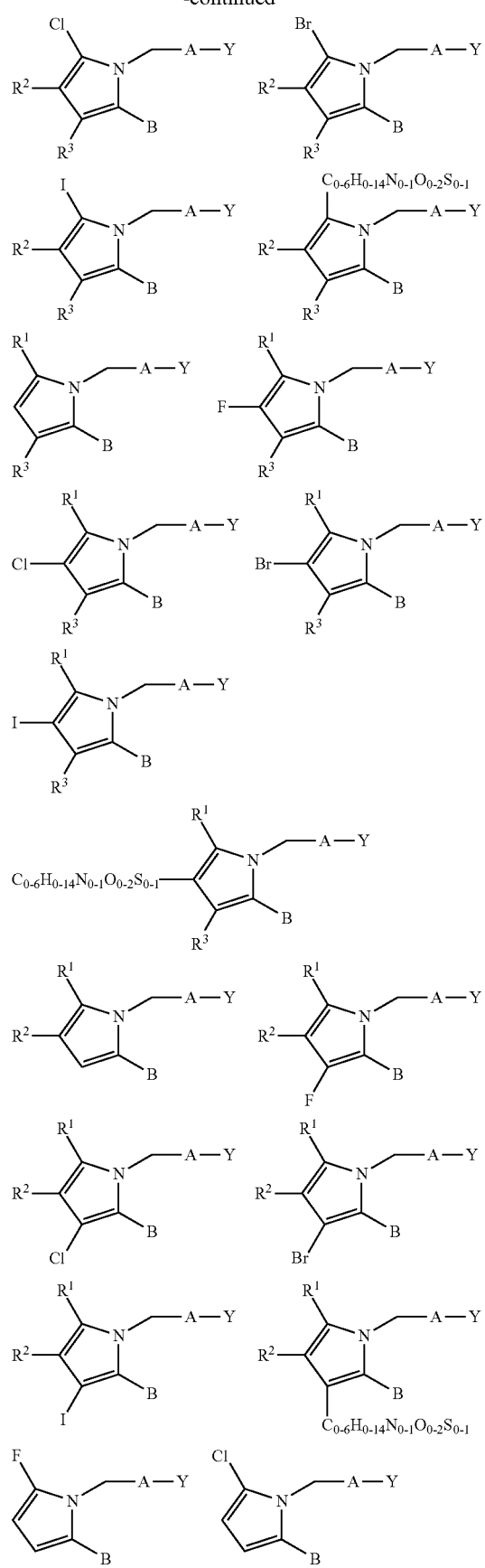

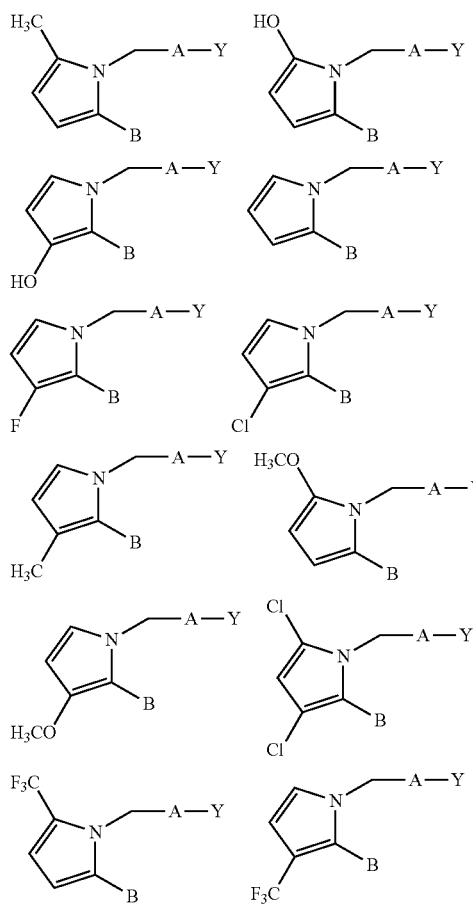

In one embodiment, $R^1$, $R^2$, and $R^3$ are acyclic, meaning that they contain no rings.

In another embodiment, $R^1$, $R^2$, and $R^3$ are independently selected from —F, —Cl, —Br, —I, —$CF_3$, —C(O)$CF_3$, —R, —C(O)R, $SO_2NR_2$, —OR, and —$NR_2$, wherein R is independently —H or $C_{1-6}$ alkyl.

B is aryl of a formula $C_{5-20}H_{0-45}N_{0-4}O_{0-4}S_{0-4}F_{0-5}Cl_{0-3}Br_{0-3}I_{0-3}$.

In another embodiment B is phenyl, pyridinyl, thienyl, or furyl, and B has 1, 2, or 3 substituents independently selected from —F, —Cl, —Br, —I, —$CF_3$, —C(O)$CF_3$, —$R^7$, —C(O)$R^7$, —$SO_2N(R^7)_2$, —$OR^7$, and —$N(R^7)_2$, wherein $R^7$ is $C_{1-10}$ alkyl with 0, 1, 2, or 3 —OH substituents, or $R^7$ is unsubstituted phenyl, pyridinyl, thienyl, or furyl.

Thus, compounds such as those below are contemplated.

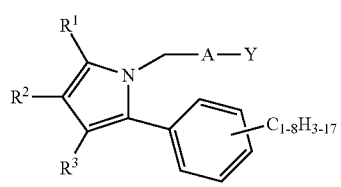

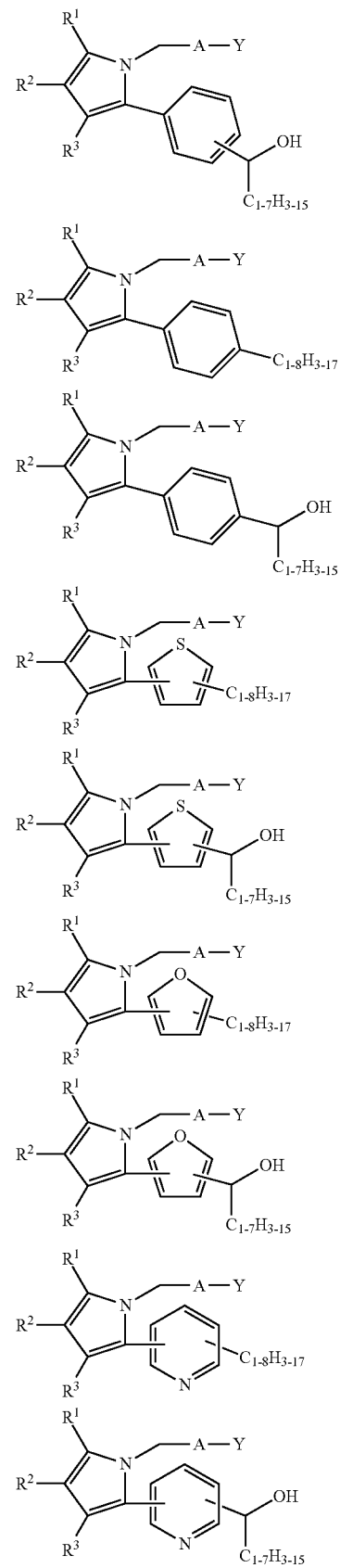

In another embodiment, B is phenyl with 1 substituent represented by:

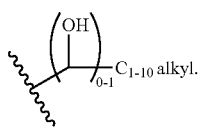

Another embodiment is a compound represented by a formula:

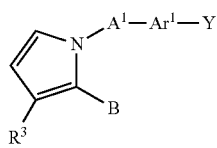

wherein $R^3$ is —H, —F, —Cl, or —Br.

Another embodiment is a compound represented by a formula:

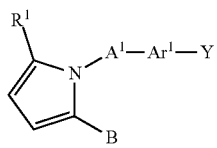

wherein $R^1$ is —H, —F, —Cl, or —Br.

In another embodiment, B is phenyl with 1 substituent having a formula $C_{2-10}H_{5-21}O_{0-2}$ which is alkyl, alkyl with 1 or two hydroxyl substituents, an ether, or a hydroxyether.

A hydroxyether is an ether with a hydroxyl substituent.

Another embodiment is a compound represented by a formula:

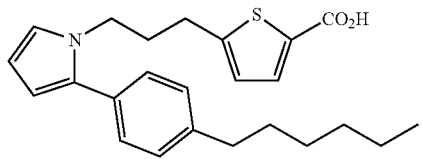

Another embodiment is a compound represented by a formula:

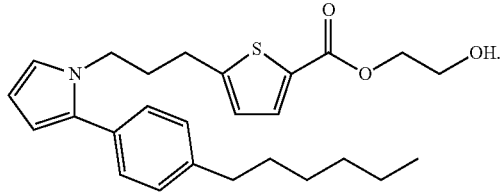 [SMILES: CCCCCCc1ccc(-c2cccn2CCCc2ccc(C(=O)OCCO)s2)cc1]

Other examples of useful compounds include:

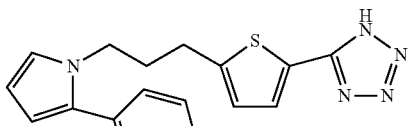

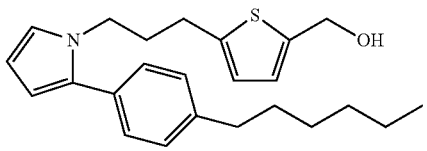

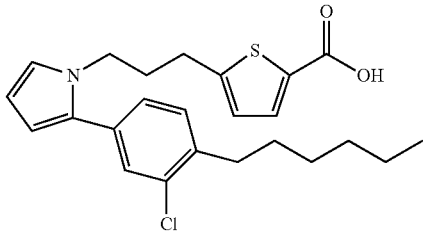

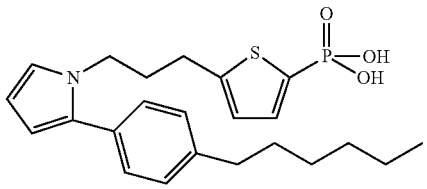

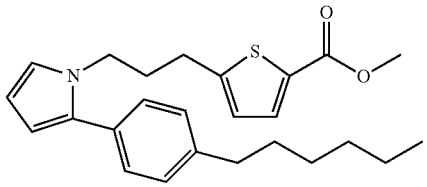

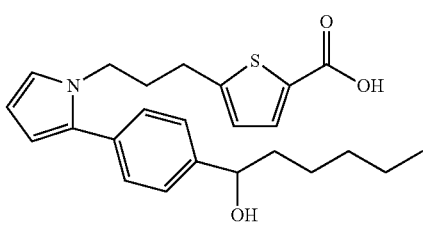

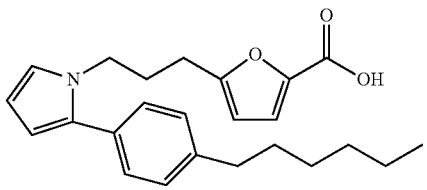

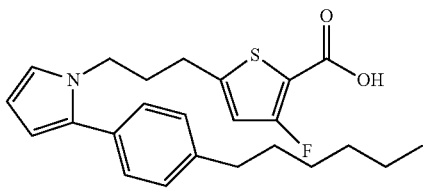

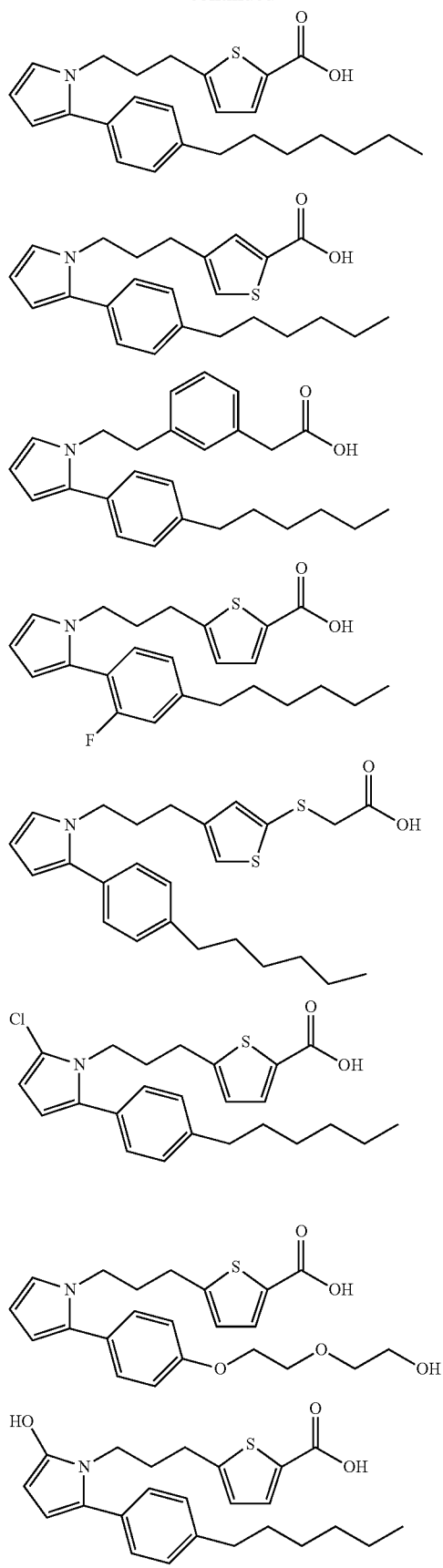
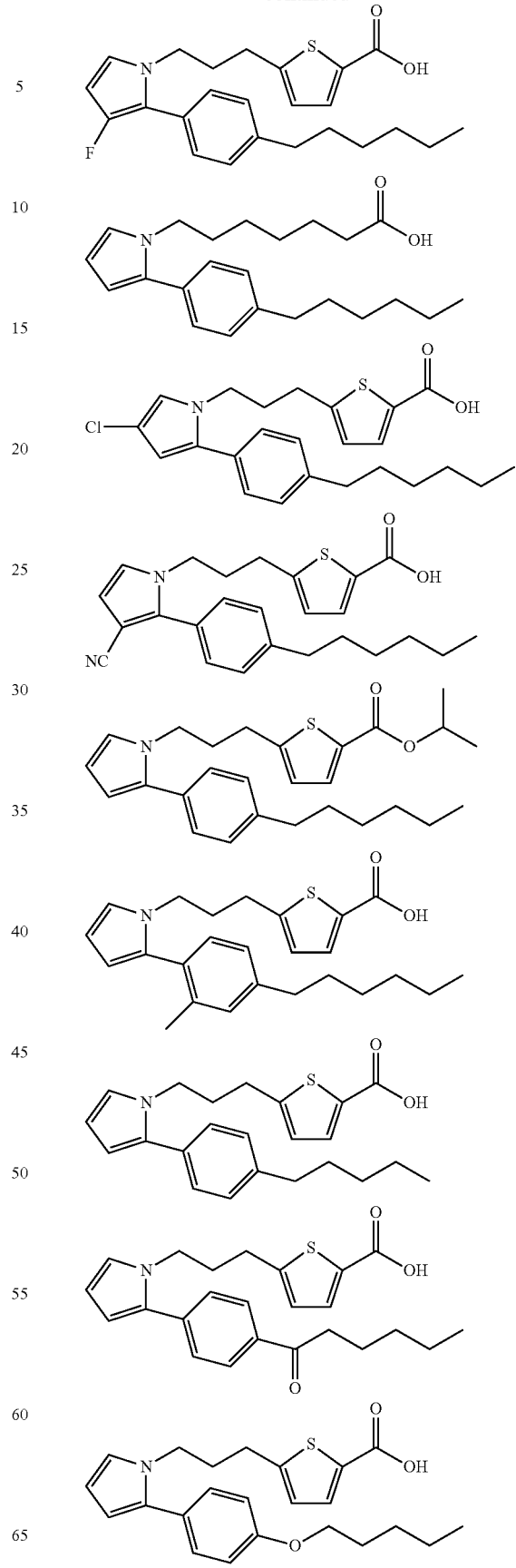

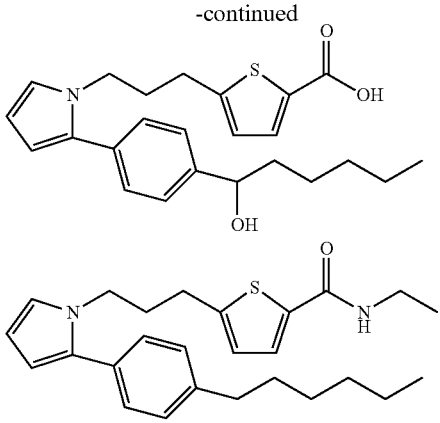

EXAMPLES

Synthetic Methods

While the compounds disclosed herein are effectively isomeric with the compounds disclosed in U.S. Pat. No. 7,985,765, the synthetic approach to each was significantly different. In the present invention, a Suzuki-Miyura reaction was needed to attach the requisite substituted aryl ring to a carbon atom of the pyrrole core structure. In the '765 patent, a Buchwald-Hartwig amination reaction was used to install the aromatic moiety onto the nitrogen atom of the pyrrole core structure. Furthermore, the compounds of the present invention are N-alkyl substituted pyrroles which, in contrast to their N-aryl pyrrole relatives, are more chemically reactive and require greater skill to handle and manipulate.

Scheme 1:

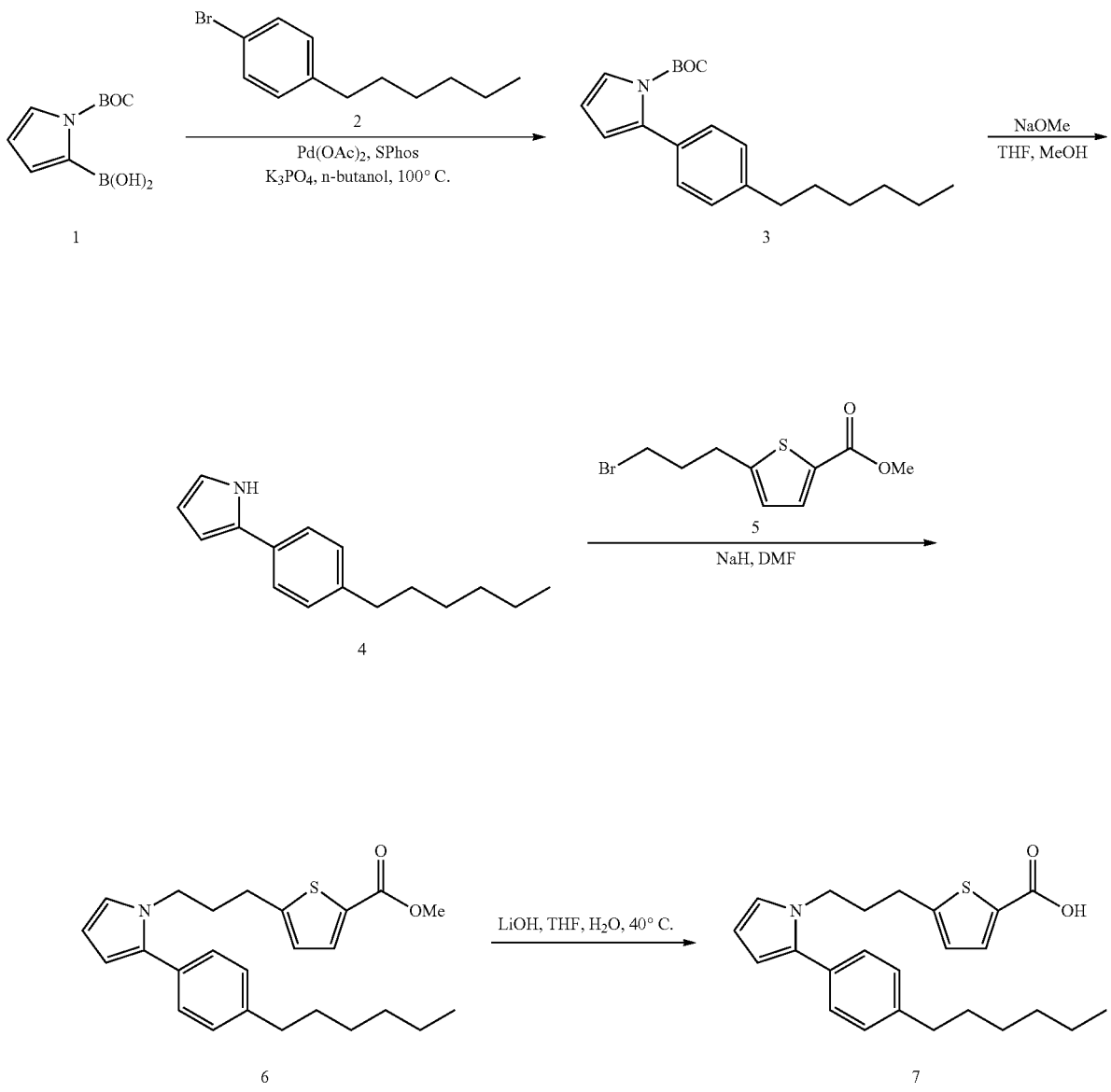

Example 1

5-(3-(2-(4-hexylphenyl)-1H-pyrrol-1-yl)propyl)thiophene-2-carboxylic acid (7)

Step 1. Coupling of 1 with 2 to give 3

Palladium acetate (2.2 mg, 0.01 mmol), 2-dicyclohexylphosphino-2',6'-dimethoxybiphenyl (SPhos, Aldrich Chemical, 8.2 mg, 0.02 mmol), potassium phosphate (212 mg, 1.0 mmol) and 1-BOC-pyrrole-2-boronic acid (1, Combi-Blocks Inc., 158 mg, 0.75 mmol) were combined in a 25 mL Schlenk tube. 1-Bromo-4-n-hexylbenzene (2, Alfa, 102 µL, 0.50 mmol) and n-butanol (Alfa, HPLC grade, 1.0 mL) were added. The reaction mixture was purged with nitrogen then the tube was sealed, placed in a 100° C. oil bath and stirred vigorously. After 18 h, the reaction was allowed to cool to room temperature, diluted with EtOAc and filtered through celite. The filtrate was concentrated in vacuo. Purification of the residue by chromatography on 12 g silica gel using a Teledyne-ISCO Combiflash machine (hexanes→20% EtOAc/hexanes, gradient) afforded 113 mg (69%) of 3.

Step 2. Deprotection of 3 to give 4

Sodium methoxide (0.2 mL of a 5.4 M solution in methanol, 1.1 mmol) was added to a solution of 3 (113 mg, 0.35 mmol) in THF (1.7 mL). After stirring overnight at room temperature, the reaction mixture was quenched by addition of saturated aqueous $NH_4Cl$ (10 mL) and extracted with EtOAc (3×20 mL). The combined organic phase was washed with water (10 mL) and brine (10 mL) then dried ($Na_2SO_4$), filtered and concentrated in vacuo. Purification of the residue by chromatography on 12 g silica gel using a Teledyne-ISCO Combiflash machine (hexanes→20% EtOAc/hexanes, gradient) afforded 58 mg (74%) of 4.

Step 3. Alkylation of 4 with 5 to give 6

Sodium hydride (13.5 mg, 60% dispersion in oil, 0.34 mmol) was added to a solution of 4 (68 mg, 0.30 mmol) in DMF (1.0 mL) at 0° C. The solution immediately turned dark red and the cooling bath was removed. After stirring for 15 min at room temperature, the mixture was re-cooled to 0° C. and methyl 5-(3-bromopropyl)thiophene-2-carboxylate (5, for example preparation, see WO94/13295, incorporated by reference herein, 90 mg, 0.34 mmol) was added as a solution in DMF (0.5 mL). The reaction mixture was allowed to warm to room temperature. After stirring for 3 d, the reaction mixture was quenched by addition of saturated aqueous $NH_4Cl$ (10 mL) and extracted with EtOAc (3×20 mL). The combined organic phase was washed with water (2×10 mL) and brine (10 mL) then dried ($Na_2SO_4$), filtered and concentrated in vacuo. Purification of the residue by chromatography on 12 g silica gel using a Teledyne-ISCO Combiflash machine (hexanes→20% EtOAc/hexanes, gradient) afforded 27 mg (22%) of 6.

Step 4. Saponification of 6 to give 7

In a 1-dram vial, ester 6 (16 mg, 0.039 mmol) was dissolved in THF (0.39 mL). Lithium hydroxide (0.20 mL of a 1.0N aqueous solution, 0.20 mmol) was added. The reaction mixture was purged with nitrogen, the vial was sealed and placed in a 40° C. oil bath and stirred vigorously. After 48 h, the reaction was allowed to cool to room temperature, and the solvents were evaporated under a stream of nitrogen. The residue was diluted with water (1 mL) and the mixture was acidified with 1 N HCl (0.5 mL). The mixture was extracted with EtOAc (3×5 mL). The combined organic phase was washed with brine (2 mL), dried ($Na_2SO_4$), filtered and concentrated in vacuo to afford 15 mg (98%) of the title compound (7).

This specific example can be readily adapted to obtain a variety of structures using synthetic methods known in the art. For example, compound 5 can be readily replaced with different bromide compounds which may be commercially available or prepared by methods known in the art. Compound 1 and compound 2 may be varied by using compounds with different substituents on the aromatic ring which may be commercially available or by utilizing electrophilic aromatic substitution methods known in the art, or the aromatic rings may be modified in compound 6 or in compound 7 to obtain a variety of compounds. Other synthetic pathways may also be used.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated. To the extent that any recitations in the incorporated references conflict with any recitations herein, the recitations herein will control.

Example 2

In Vitro Testing

US 2007/0129552, incorporated by reference herein in its entirety, describes the methods used to obtain the in vitro data in the table below.

TABLE 1

| Example | Structure | EP2 data | | | EP4 data | | Other Receptors (EC50 in nM) | | | | | |
| --- | --- | --- | --- | --- | --- | --- | --- | --- | --- | --- | --- | --- |
| | | flipr EC50 | cAMP EC50 | Ki | flipr EC50 | Ki | hFP | hEP1 | hEP3A | hTP | hIP | hDP |
| 1 | (structure) | 998 | 3 | 23 | >10000 | 2659 | NA | NA | NA | NA | NA | NA |

What is claimed is:

1. A compound represented by the formula:

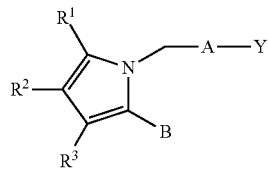

or a pharmaceutically acceptable salt thereof, wherein
Y is —$CO_2R^4$, —$CONR^5R^6$, —$CON(CH_2CH_2OH)_2$, —$CONH(CH_2CH_2OH)$, —$CH_2OH$, —$P(O)(OH)_2$, —$CONHSO_2R^4$, —$SO_2NR^5R^6$,

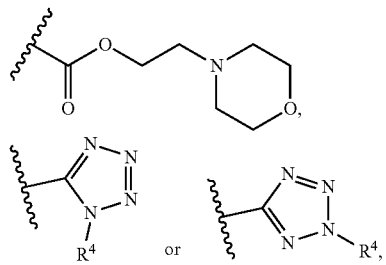

wherein $R^4$, $R^5$, and $R^6$ are independently H, $C_1$-$C_6$ alkyl, $C_{1-6}$ hydroxyalkyl, unsubstituted phenyl, or unsubstituted biphenyl;

A is —$(CH_2)_5$—, —CH=CH$(CH_2)_3$—, or —C≡C$(CH_2)_3$—, wherein:
 a) one or two —$CH_2$— may be replaced with —O— or —S—, or
 b) —$CH_2CH_2$—, —$(CH_2)_3$—, or —$(CH_2)_4$— is replaced by —Ar— and one —$CH_2$— may be replaced by —O— or —S—;

Ar is 1,3-attached thienyl, furyl, or pyrrolyl with zero, one, or two substituents selected from, —F, —Cl, —Br, —$CH_3$, or —$OCH_3$;

$R^1$, $R^2$, and $R^3$ are independently —H, —F, —Cl, —Br, —I, —$CF_3$, —$C(O)CF_3$, —R, —C(O)R, —$SO_2NR_2$, —OR, or —$NR_2$, wherein R is independently —H or $C_{1-6}$ alkyl B is phenyl, pyridinyl, thienyl, or furyl, and B has one, two, or three substituents independently selected from —F, —Cl, —Br, —I, —$CF_3$, —$C(O)CF_3$, —$R^7$, —$C(O)R^7$, —$SO_2N(R^7)_2$, —$OR^7$, and —$N(R^7)_2$, wherein $R^7$ is $C_{1-10}$ alkyl with 0, 1, 2, or 3 —OH substituents, or $R^7$ is unsubstituted phenyl, pyridinyl, thienyl, or furyl.

2. The compound of claim 1 wherein $R^3$ is —H, —F, —Cl, or —Br.

3. The compound of claim 1 wherein B is phenyl with one substituent represented by:

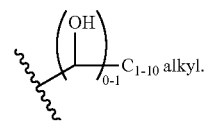

4. The compound of claim 1 wherein Y is —$CO_2R^4$, wherein $R^4$ is —H or $C_{1-6}$ alkyl.

5. The compound of claim 1 wherein $R^1$ is —H, —F, —Cl, or —Br.

6. The compound of claim 1 represented by a formula:

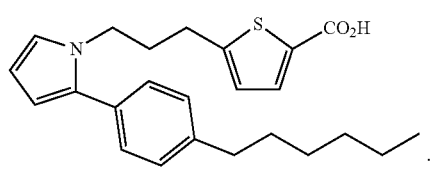 [SMILES: CCCCCCc1ccc(-c2cccn2CCCc2ccc(C(=O)O)s2)cc1]

7. The compound of claim 1 wherein Y is:
—$CO_2(CH_2)_2OH$ or

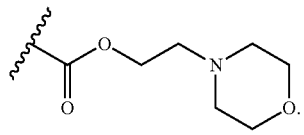 [SMILES: *C(=O)OCCN1CCOCC1]

8. The compound of claim 7 represented by a formula:

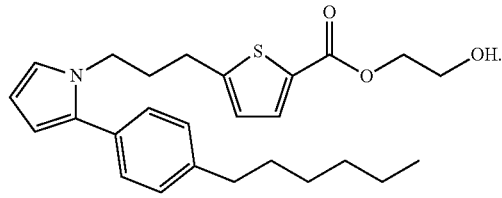 [SMILES: CCCCCCc1ccc(-c2cccn2CCCc2ccc(C(=O)OCCO)s2)cc1]

9. A pharmaceutical composition comprising a compound according to claim 1 and one or more pharmaceutically acceptable excipients.

10. A method of reducing intraocular pressure, therapeutically treating glaucoma or intraocular pressure, growing hair, or improving the appearance of hair, comprising administering a compound according to claim 1 to a mammal in need thereof.

11. The method of claim 10 wherein the mammal is a human being.

* * * * *

UNITED STATES PATENT AND TRADEMARK OFFICE
CERTIFICATE OF CORRECTION

PATENT NO. : 9,637,477 B2
APPLICATION NO. : 14/716478
DATED : May 2, 2017
INVENTOR(S) : David W. Old Page 1 of 2

It is certified that error appears in the above-identified patent and that said Letters Patent is hereby corrected as shown below:

In the Specification

In Column 1, Line 7, delete "No." and insert -- no. --, therefor.

In Column 1, Line 27, after "disorders" insert -- . --.

In Column 2, Lines 3-8, delete "Growing hair includes increasing the length or radius of individual hairs as well as increasing the number of hairs present in a given area. Improving the appearance of hair includes improving the color, such as darkening, or improving its gloss, shine, or other properties related to the reflection, absorption, emission, or dispersion of light." and insert the same on Column 2, Line 2, as a continuation of the same paragraph.

In Column 4, Line 10, delete "galactunoric" and insert -- galacturonic --, therefor.

In Column 5, Line 54, delete "akynyl;" and insert -- alkynyl; --, therefor.

In Column 7, Line 4, delete "hydroflourocarbons" and insert -- hydrofluorocarbons --, therefor.

In Column 7, Line 8, delete "substitutents" and insert -- substituents --, therefor.

In Column 7, Line 55, after "—$SO_2NR^5R^6$" insert -- , --.

In Column 8, Line 24, delete "—S—," and insert -- —S—. --, therefor.

In Column 8, Lines 25-26, delete "$C_{3-10}H_{0-23}N_{0-4}O_{0-4}S_{0-4}F_{0-5}Cl_{0-3}Br_{0-3}I_{0-3}$," and insert -- $C_{3-10}H_{0-23}N_{0-4}O_{0-4}S_{0-4}F_{0-5}Cl_{0-3}Br_{0-3}I_{0-3}$. --, therefor.

In Column 11, Line 26, delete "—S—," and insert -- —S—. --, therefor.

Signed and Sealed this
Twentieth Day of June, 2017

Joseph Matal
*Performing the Functions and Duties of the
Under Secretary of Commerce for Intellectual Property and
Director of the United States Patent and Trademark Office*

CERTIFICATE OF CORRECTION (continued) Page 2 of 2
U.S. Pat. No. 9,637,477 B2

In Column 23, Lines 32-42, delete " 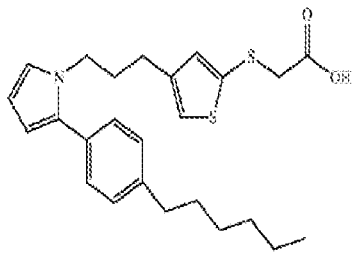 "

and insert -- 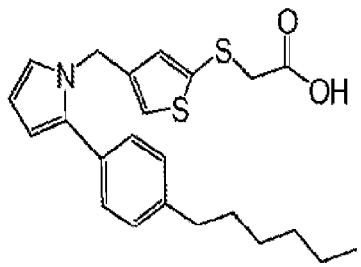 --, therefor.

In Column 26, Line 3, delete "Suzuki-Miyura" and insert -- Suzuki-Miyaura --, therefor.

In Column 27, Line 29, delete "NH$_4$Cl'" and insert -- NH$_4$Cl --, therefor.

In Column 28, Line 10, delete "1.0N" and insert -- 1.0 N --, therefor.

In the Claims

In Column 29, Line 30, in Claim 1, delete "R$^4$'" and insert -- R$^4$, --, therefor.

In Column 30, Line 10, in Claim 5, delete "R$^1$is" and insert -- R$^1$ is --, therefor.